(12) United States Patent
Slone et al.

(10) Patent No.: US 9,282,996 B2
(45) Date of Patent: Mar. 15, 2016

(54) EXTRA-ARTICULAR IMPLANTABLE MECHANICAL ENERGY ABSORBING ASSEMBLIES

(71) Applicant: Moximed, Inc., Hayward, CA (US)

(72) Inventors: Clinton N. Slone, San Francisco, CA (US); Toru Mino, Somerville, MA (US)

(73) Assignee: MOXIMED, INC., Hayward, CA (US)

( * ) Notice: Subject to any disclaimer, the term of this patent is extended or adjusted under 35 U.S.C. 154(b) by 0 days.

(21) Appl. No.: 14/205,958

(22) Filed: Mar. 12, 2014

(65) Prior Publication Data

US 2014/0277445 A1    Sep. 18, 2014

Related U.S. Application Data

(60) Provisional application No. 61/779,311, filed on Mar. 13, 2013.

(51) Int. Cl.
*A61F 2/08*   (2006.01)
*A61B 17/56*  (2006.01)
*A61F 2/48*   (2006.01)

(52) U.S. Cl.
CPC ........... *A61B 17/56* (2013.01); *A61B 2017/567* (2013.01); *A61F 2002/485* (2013.01)

(58) Field of Classification Search
CPC ....... A61F 2/30; A61F 2002/485; A61F 2/08; A61F 2002/484; A61F 2002/5006; A61F 2002/501; A61F 2002/3055; A61F 2002/502; A61F 2002/5032; A61F 2002/5033; A61F 2002/507; A61B 2017/567; A61B 17/60; A61B 17/56
USPC ............................ 623/13.11–13.2, 37, 49–50, 623/17.11–17.16; 606/257–259
See application file for complete search history.

(56) References Cited

U.S. PATENT DOCUMENTS

| 3,294,391 | A | * | 12/1966 | Smith | F16F 9/003 188/297 |
| 3,779,654 | A | * | 12/1973 | Horne | 403/62 |
| 4,271,938 | A | * | 6/1981 | Berger | F16F 9/19 188/280 |
| 4,440,273 | A | * | 4/1984 | Butler | F16F 9/43 137/513.7 |

(Continued)

FOREIGN PATENT DOCUMENTS

WO       WO02/078554      10/2002

OTHER PUBLICATIONS

International Search Report and Written Opinion for PCT Patent App. No. PCT/ US2014/024164 (Aug. 6, 2014).

*Primary Examiner* — Alvin Stewart
(74) *Attorney, Agent, or Firm* — Adam J. Cermak; Cermak Nakajima & McGowan LLP

(57) ABSTRACT

Implantable assemblies/devices and methods for manipulating energy transferred by members defining an anatomical joint, wherein the members collectively define a path of motion. Assemblies/devices are provided with a first component configured to be attached to a first member of the anatomical joint, a second component configured to be attached to a second member of the anatomical joint; and a hydraulic member joining the first and second components. The hydraulic member is placed under compression to absorb energy transferred by the members when the first component is attached to the first member and the second component is attached to the second member and a distance between locations of attachment of the first and second components becomes smaller then a predefined distance between the locations.

17 Claims, 11 Drawing Sheets

(56) References Cited

U.S. PATENT DOCUMENTS

| | | | | |
|---|---|---|---|---|
| 4,637,382 A * | 1/1987 | Walker | | 606/55 |
| 4,746,106 A * | 5/1988 | Fukumura | | F16F 9/468 |
| | | | | 267/218 |
| 4,788,489 A * | 11/1988 | Kobayashi | | B60G 17/01933 |
| | | | | 280/735 |
| 4,874,185 A * | 10/1989 | Kijima | | B60G 7/02 |
| | | | | 280/124.139 |
| 4,890,822 A * | 1/1990 | Ezure | | F16F 9/088 |
| | | | | 188/318 |
| 4,932,975 A * | 6/1990 | Main et al. | | 623/17.12 |
| 5,015,002 A * | 5/1991 | Goodman | | F16J 3/042 |
| | | | | 139/109 |
| 5,375,823 A * | 12/1994 | Navas | | 623/17.15 |
| 5,423,816 A * | 6/1995 | Lin | | 606/247 |
| 5,695,496 A * | 12/1997 | Orsak et al. | | 606/54 |
| 6,120,547 A * | 9/2000 | Christensen | | A61F 2/66 |
| | | | | 623/38 |
| 6,162,223 A * | 12/2000 | Orsak et al. | | 606/59 |
| 6,193,225 B1 * | 2/2001 | Watanabe | | 267/180 |
| 6,511,512 B2 * | 1/2003 | Phillips et al. | | 623/27 |
| 6,540,708 B1 * | 4/2003 | Manspeizer | | 602/16 |
| 6,835,207 B2 * | 12/2004 | Zacouto et al. | | 623/17.12 |
| 6,969,408 B2 * | 11/2005 | Lecomte | | A61F 2/66 |
| | | | | 623/55 |
| 6,981,989 B1 * | 1/2006 | Fleischmann | | A61F 2/442 |
| | | | | 623/17.11 |
| 7,029,475 B2 * | 4/2006 | Panjabi | | 606/279 |
| 7,291,150 B2 * | 11/2007 | Graf | | 606/86 A |
| 7,361,196 B2 * | 4/2008 | Fallin et al. | | 623/61 |
| 7,371,262 B2 * | 5/2008 | Lecomte | | A61F 2/66 |
| | | | | 623/49 |
| 7,476,238 B2 * | 1/2009 | Panjabi | | 606/257 |
| 7,611,540 B2 * | 11/2009 | Clifford et al. | | 623/20.21 |
| 7,655,041 B2 * | 2/2010 | Clifford et al. | | 623/13.12 |
| 7,744,653 B2 * | 6/2010 | Rush et al. | | 623/34 |
| 8,025,680 B2 * | 9/2011 | Hayes et al. | | 606/257 |
| 8,029,574 B2 * | 10/2011 | Kellar et al. | | 623/23.41 |
| 8,070,813 B2 * | 12/2011 | Grotz | | A61F 2/4465 |
| | | | | 623/17.11 |
| 8,088,166 B2 * | 1/2012 | Makower et al. | | 623/20.14 |
| 8,100,967 B2 * | 1/2012 | Makower et al. | | 623/13.12 |
| 8,123,805 B2 * | 2/2012 | Makower et al. | | 623/13.12 |
| 8,409,281 B2 * | 4/2013 | Makower et al. | | 623/13.12 |
| 8,523,948 B2 * | 9/2013 | Slone et al. | | 623/18.11 |
| 8,679,178 B2 * | 3/2014 | Slone et al. | | 623/13.12 |
| 8,709,090 B2 * | 4/2014 | Makower et al. | | 623/20.21 |
| 8,801,795 B2 * | 8/2014 | Makower et al. | | 623/20.21 |
| 8,845,724 B2 * | 9/2014 | Shenoy et al. | | 623/13.12 |
| 8,894,714 B2 * | 11/2014 | Makower et al. | | 623/20.21 |
| 8,992,620 B2 * | 3/2015 | Ashley et al. | | 623/17.16 |
| 9,005,298 B2 * | 4/2015 | Makower et al. | | 623/20.14 |
| 2002/0120349 A1 * | 8/2002 | Phillips | | A61F 2/60 |
| | | | | 623/35 |
| 2002/0151978 A1 * | 10/2002 | Zacouto et al. | | 623/17.12 |
| 2002/0177906 A1 * | 11/2002 | Phillips | | A61F 2/60 |
| | | | | 623/27 |
| 2004/0059423 A1 * | 3/2004 | Barnes et al. | | 623/18.12 |
| 2004/0260302 A1 * | 12/2004 | Manspeizer | | 606/90 |
| 2005/0049708 A1 * | 3/2005 | Atkinson et al. | | 623/17.16 |
| 2006/0064169 A1 * | 3/2006 | Ferree | | 623/17.12 |
| 2007/0043356 A1 * | 2/2007 | Timm et al. | | 606/61 |
| 2007/0233254 A1 * | 10/2007 | Grotz et al. | | 623/17.11 |
| 2008/0058930 A1 * | 3/2008 | Edie | | A61F 2/44 |
| | | | | 623/17.11 |
| 2008/0275509 A1 * | 11/2008 | Clifford et al. | | 606/282 |
| 2008/0275552 A1 * | 11/2008 | Makower et al. | | 623/13.13 |
| 2008/0275555 A1 * | 11/2008 | Makower et al. | | 623/14.12 |
| 2008/0275558 A1 * | 11/2008 | Clifford et al. | | 623/20.14 |
| 2008/0275561 A1 * | 11/2008 | Clifford et al. | | 623/20.21 |
| 2008/0275562 A1 * | 11/2008 | Clifford et al. | | 623/20.21 |
| 2008/0275563 A1 * | 11/2008 | Makower et al. | | 623/20.21 |
| 2009/0014016 A1 * | 1/2009 | Clifford et al. | | 128/898 |
| 2009/0275945 A1 * | 11/2009 | Makower et al. | | 606/60 |
| 2009/0318976 A1 * | 12/2009 | Gabriel et al. | | 606/283 |
| 2010/0145449 A1 * | 6/2010 | Makower et al. | | 623/13.14 |
| 2010/0204794 A1 * | 8/2010 | Jarzem | | A61B 17/8805 |
| | | | | 623/17.12 |
| 2011/0087297 A1 * | 4/2011 | Orbay et al. | | 606/328 |
| 2011/0093079 A1 * | 4/2011 | Slone et al. | | 623/18.11 |
| 2011/0093080 A1 * | 4/2011 | Slone et al. | | 623/20.14 |
| 2011/0112639 A1 * | 5/2011 | Regala et al. | | 623/13.12 |
| 2011/0213466 A1 | 9/2011 | Shenoy et al. | | |
| 2011/0245928 A1 * | 10/2011 | Landry et al. | | 623/20.28 |
| 2011/0264216 A1 * | 10/2011 | Makower et al. | | 623/13.12 |
| 2012/0022655 A1 * | 1/2012 | Clifford | | 623/18.11 |
| 2012/0046754 A1 * | 2/2012 | Clifford et al. | | 623/22.11 |
| 2012/0053644 A1 * | 3/2012 | Landry et al. | | 606/86 R |
| 2012/0123551 A1 * | 5/2012 | Landry et al. | | 623/20.21 |
| 2012/0143189 A1 * | 6/2012 | Wolfson | | 606/55 |
| 2012/0253414 A1 * | 10/2012 | Gabriel et al. | | 606/86 R |
| 2012/0296434 A1 * | 11/2012 | Kumar | | 623/18.11 |
| 2013/0013066 A1 * | 1/2013 | Landry et al. | | 623/14.12 |
| 2013/0013067 A1 * | 1/2013 | Landry et al. | | 623/14.12 |
| 2013/0018479 A1 * | 1/2013 | Grotz | | 623/22.14 |
| 2013/0138218 A1 * | 5/2013 | Landry et al. | | 623/20.14 |
| 2013/0166036 A1 * | 6/2013 | De Cortanze et al. | | 623/20.23 |
| 2013/0261670 A1 * | 10/2013 | Laeng et al. | | 606/281 |
| 2013/0304208 A1 * | 11/2013 | Clifford et al. | | 623/13.12 |
| 2013/0325122 A1 * | 12/2013 | Gabriel et al. | | 623/13.12 |
| 2013/0325123 A1 * | 12/2013 | Clifford et al. | | 623/13.12 |
| 2014/0156021 A1 * | 6/2014 | Makower et al. | | 623/23.41 |
| 2014/0243997 A1 * | 8/2014 | Clausen | | A61F 2/66 |
| | | | | 623/55 |
| 2014/0257292 A1 * | 9/2014 | Embleton et al. | | 606/71 |
| 2014/0257501 A1 * | 9/2014 | Lowe et al. | | 623/20.22 |
| 2014/0277445 A1 * | 9/2014 | Slone et al. | | 623/13.12 |
| 2014/0277446 A1 * | 9/2014 | Clifford et al. | | 623/13.12 |
| 2014/0277533 A1 * | 9/2014 | Slone et al. | | 623/20.24 |

* cited by examiner

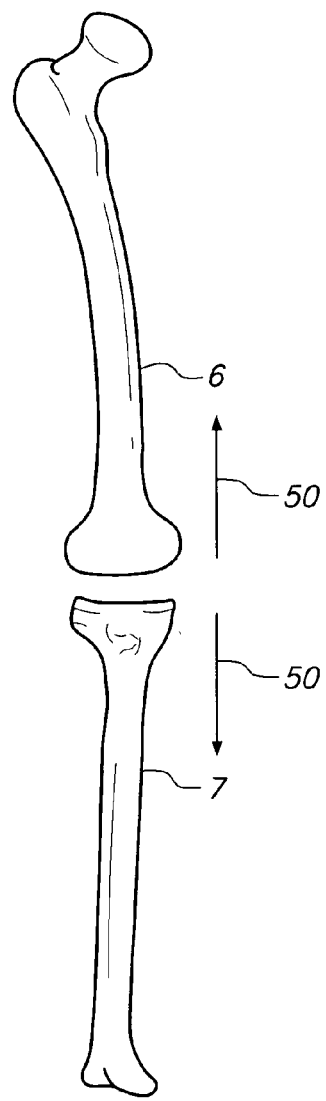 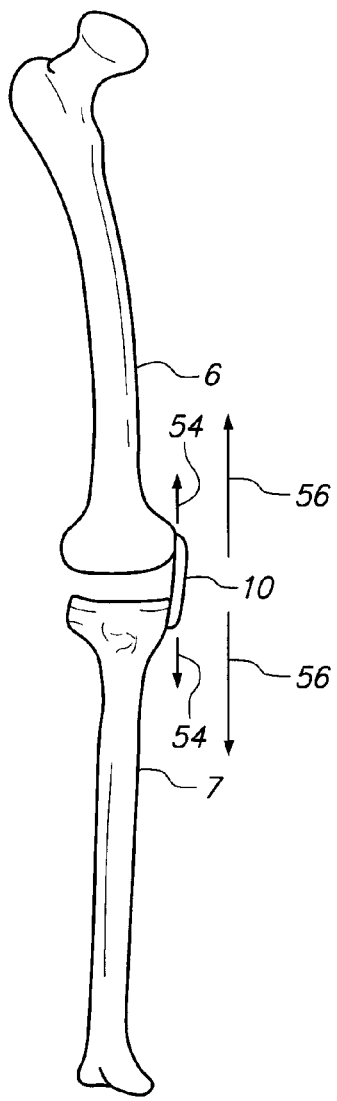

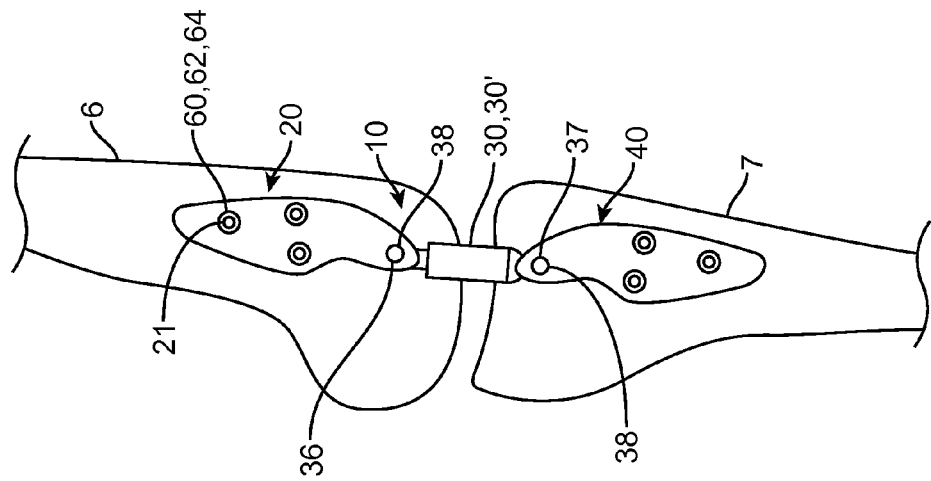
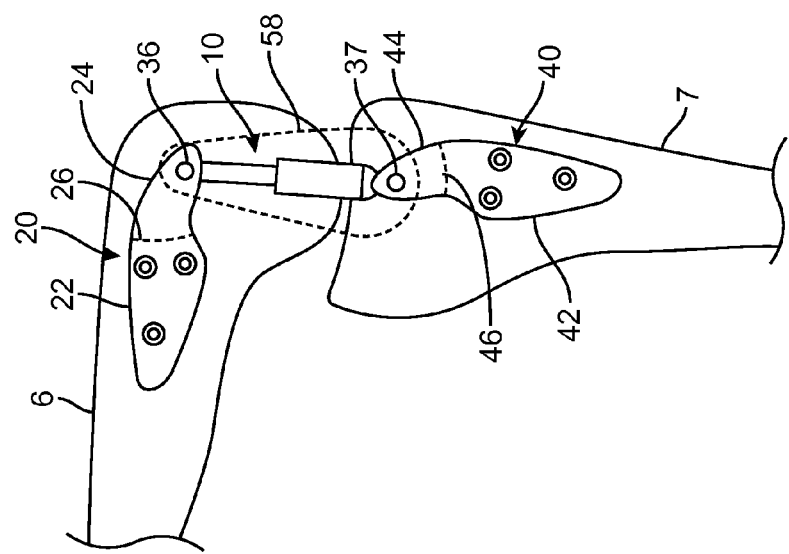

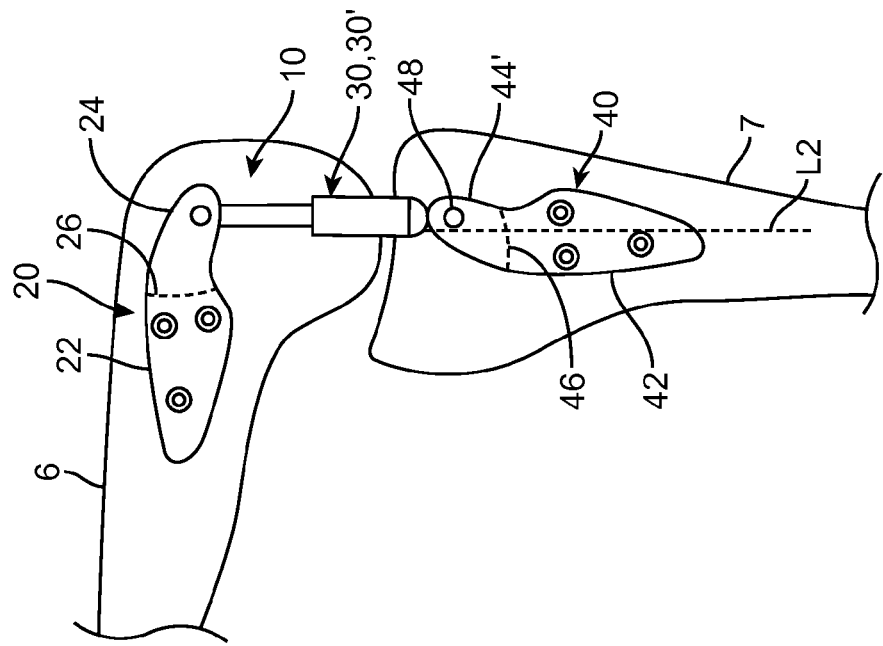
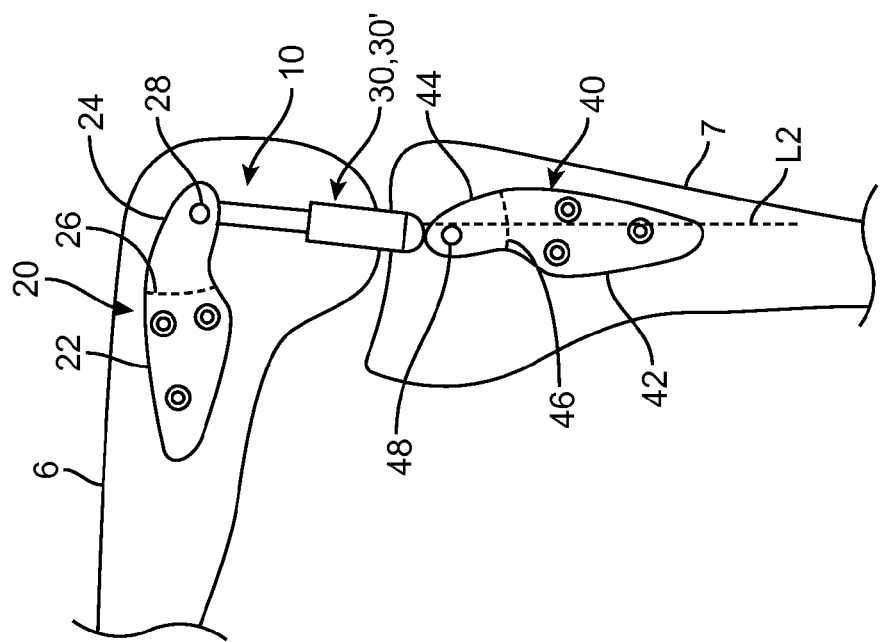

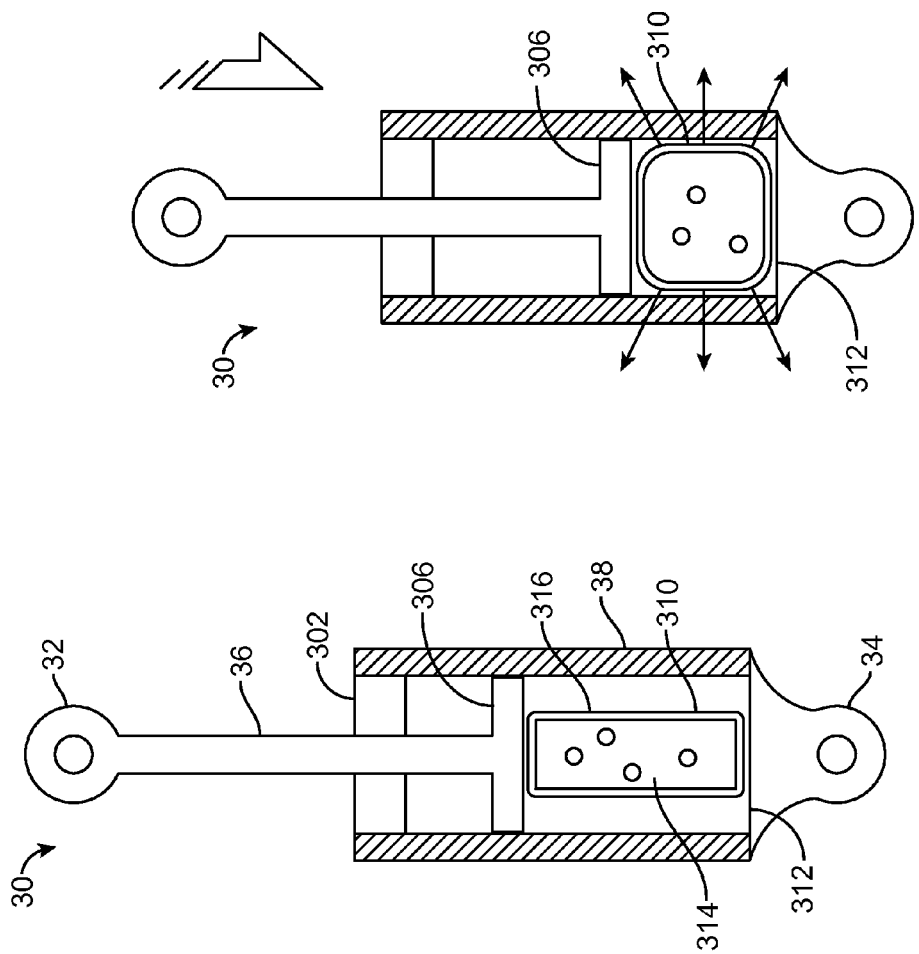

EXTRA-ARTICULAR IMPLANTABLE MECHANICAL ENERGY ABSORBING ASSEMBLIES

This application claims priority under 35 U.S.C. §119 to U.S. Provisional App. No. 61/799,311, filed 13 Mar. 2013, the entirety of which is incorporated by reference herein.

FIELD OF THE INVENTION

The present invention is directed towards systems and methods for treating tissue of a body and more particularly, towards approaches designed to reduce mechanical energy transferred between members forming a natural joint.

BACKGROUND OF THE INVENTION

A joint is the location at which two or more bones make contact. They are constructed to allow movement and provide mechanical support, and are classified structurally and functionally. Structural classification is determined by how the bones connect to each other, while functional classification is determined by the degree of movement between the articulating bones. In practice, there is significant overlap between the two types of classifications.

There are three structural classifications of joints, namely fibrous or immovable joints, cartilaginous joints and synovial joints. Fibrous/Immovable bones are connected by dense connective tissue, consisting mainly of collagen. The fibrous joints are further divided into three types:

- sutures which are found between bones of the skull;
- syndesmosis which are found between long bones of the body; and
- gomphosis which is a joint between the root of a tooth and the sockets in the maxilla or mandible.

With cartilaginous joints, bones are connected entirely by cartilage (also known as "synchondroses"). Cartilaginous joints allow more movement between bones than a fibrous joint but less than the highly mobile synovial joint. Synovial joints have a space between the articulating bones for synovial fluid. This classification contains joints that are the most mobile of the three, and includes the knee and shoulder. These are further classified into ball and socket joints, condyloid joints, saddle joints, hinge joints, pivot joints, and gliding joints.

Joints can also be classified functionally, by the degree of mobility they allow. Synarthrosis joints permit little or no mobility. They can be categorized by how the two bones are joined together. That is, synchrondoses are joints where the two bones are connected by a piece of cartilage. Synostoses are where two bones that are initially separated eventually fuse together as a child approaches adulthood. By contrast, amphiarthrosis joints permit slight mobility. The two bone surfaces at the joint are both covered in hyaline cartilage and joined by strands of fibrocartilage. Most amphiarthrosis joints are cartilaginous.

Finally, diarthrosis joints permit a variety of movements (e.g. flexion, adduction, pronation). Only synovial joints are diarthrodial and they can be divided into six classes: 1. ball and socket—such as the shoulder or the hip and femur; 2. hinge—such as the elbow; 3. pivot—such as the radius and ulna; 4. condyloidal (or ellipsoidal)—such as the wrist between radius and carpals, or knee; 5. saddle—such as the joint between carpal thumbs and metacarpals; and 6. gliding—such as between the carpals.

Synovial joints (or diarthroses, or diarthroidal joints) are the most common and most moveable type of joints in the body. As with all other joints in the body, synovial joints achieve movement at the point of contact of the articulating bones. Structural and functional differences distinguish the synovial joints from the two other types of joints in the body, with the main structural difference being the existence of a cavity between the articulating bones and the occupation of a fluid in that cavity which aids movement. The whole of a diarthrosis is contained by a ligamentous sac, the joint capsule or articular capsule. The surfaces of the two bones at the joint are covered in cartilage. The thickness of the cartilage varies with each joint, and sometimes may be of uneven thickness. Articular cartilage is multi-layered. A thin superficial layer provides a smooth surface for the two bones to slide against each other. Of all the layers, it has the highest concentration of collagen and the lowest concentration of proteoglycans, making it very resistant to shear stresses. Deeper than that is an intermediate layer, which is mechanically designed to absorb shocks and distribute the load efficiently. The deepest layer is highly calcified, and anchors the articular cartilage to the bone. In joints where the two surfaces do not fit snugly together, a meniscus or multiple folds of fibro-cartilage within the joint correct the fit, ensuring stability and the optimal distribution of load forces. The synovium is a membrane that covers all the non-cartilaginous surfaces within the joint capsule. It secretes synovial fluid into the joint, which nourishes and lubricates the articular cartilage. The synovium is separated from the capsule by a layer of cellular tissue that contains blood vessels and nerves.

Cartilage is a type of dense connective tissue and as noted above, it forms a critical part of the functionality of a body joint. It is composed of collagenous fibers and/or elastin fibers, and cells called chondrocytes, all of which are embedded in a firm gel-like ground substance called the matrix. Articular cartilage is avascular (contains no blood vessels) and nutrients are diffused through the matrix. Cartilage serves several functions, including providing a framework upon which bone deposition can begin and supplying smooth surfaces for the movement of articulating bones. Cartilage is found in many places in the body including the joints, the rib cage, the ear, the nose, the bronchial tubes and between intervertebral discs. There are three main types of cartilage: hyaline, elastic and fibrocartilage.

Chondrocytes are the only cells found in cartilage. They produce and maintain the cartilaginous matrix. Experimental evidence indicates that cells are sensitive to their mechanical (stress-strain) state, and react directly to mechanical stimuli. The biosynthetic response of chondrocytes was found to be sensitive to the frequency and amplitude of loading (Wong et al., 1999 and Kurz et al., 2001). Recent experimental studies further indicate that excessive, repetitive loading may induce cell death, and cause morphological and cellular damage, as seen in degenerative joint disease (Lucchinetti et al., 2002 and Sauerland et al., 2003). Islam et al. (2002) found that continuous cyclic hydrostatic pressure (5 MPa, 1 Hz for 4 hours) induced apoptosis in human chondrocytes derived from osteoarthritic cartilage in vitro. In contrast, cyclic, physiological-like loading was found to trigger a partial recovery of morphological and ultra-structural aspects in osteoarthritic human articular chondrocytes (Nerucci et al., 1999).

Cancellous bone (also known as trabecular, or spongy) is a type of osseous tissue which also forms an important aspect of a body joint. Cancellous bone has a low density and strength but very high surface area, that fills the inner cavity of long bones. The external layer of cancellous bone contains red bone marrow where the production of blood cellular components (known as hematopoiesis) takes place. Cancellous bone is also where most of the arteries and veins of bone organs are found. The second type of osseous tissue is known as cortical bone, forming the hard outer layer of bone organs.

Various maladies can affect the joints, one of which is arthritis. Arthritis is a group of conditions where there is damage caused to the joints of the body. Arthritis is the leading cause of disability in people over the age of 65.

There are many forms of arthritis, each of which has a different cause. Rheumatoid arthritis and psoriatic arthritis are autoimmune diseases in which the body is attacking itself. Septic arthritis is caused by joint infection. Gouty arthritis is caused by deposition of uric acid crystals in the joint that results in subsequent inflammation. The most common form of arthritis, osteoarthritis is also known as degenerative joint disease and occurs following trauma to the joint, following an infection of the joint or simply as a result of aging.

Unfortunately, all arthritides feature pain. Patterns of pain differ among the arthritides and the location. Rheumatoid arthritis is generally worse in the morning; in the early stages, patients often do not have symptoms following their morning shower.

Osteoarthritis (OA, also known as degenerative arthritis or degenerative joint disease, and sometimes referred to as "arthrosis" or "osteoarthrosis" or in more colloquial terms "wear and tear"), is a condition in which low-grade inflammation results in pain in the joints, caused by wearing of the cartilage that covers and acts as a cushion inside joints. As the bone surfaces become less well protected by cartilage, the patient experiences pain upon weight bearing, including walking and standing. Due to decreased movement because of the pain, regional muscles may atrophy, and ligaments may become more lax. OA is the most common form of arthritis.

The main symptoms of osteoarthritis are chronic pain, causing loss of mobility and often stiffness. "Pain" is generally described as a sharp ache, or a burning sensation in the associated muscles and tendons. OA can cause a crackling noise (called "crepitus") when the affected joint is moved or touched, and patients may experience muscle spasm and contractions in the tendons. Occasionally, the joints may also be filled with fluid. Humid weather increases the pain in many patients.

OA commonly affects the hand, feet, spine, and the large weight-bearing joints, such as the hips and knees, although in theory, any joint in the body can be affected. As OA progresses, the affected joints appear larger, are stiff and painful, and usually feel worse, the more they are used and loaded throughout the day, thus distinguishing it from rheumatoid arthritis. With progression in OA, cartilage loses its viscoelastic properties and its ability to absorb load.

Generally speaking, the process of clinically detectable osteoarthritis is irreversible, and typical treatment consists of medication or other interventions that can reduce the pain of OA and thereby improve the function of the joint. According to an article entitled "Surgical approaches for osteoarthritis" by Klaus-Peter Günther, MD, over recent decades, a variety of surgical procedures have been developed with the aim of decreasing or eliminating pain and improving function in patients with advanced osteoarthritis (OA). The different approaches include preservation or restoration of articular surfaces, total joint replacement with artificial implants, and arthrodeses.

Arthrodeses are described as being reasonable alternatives for treating OA of small hand and foot joints as well as degenerative disorders of the spine, but were deemed to be rarely indicated in large weight-bearing joints such as the knee due to functional impairment of gait, cosmetic problems and further side-effects. Total joint replacement was characterized as an extremely effective treatment for severe joint disease. Moreover, recently developed joint-preserving treatment modalities were identified as having a potential to stimulate the formation of a new articular surface in the future. However, it was concluded that such techniques do not presently predictably restore a durable articular surface to an osteoarthritic joint. Thus, the correction of mechanical abnormalities by osteotomy and joint debridement are still considered as treatment options in many patients. Moreover, patients with limb malalignment, instability and intra-articular causes of mechanical dysfunction can benefit from an osteotomy to provide pain relief, with the goal being the transfer of weight-bearing forces from arthritic portions to healthier locations of a joint.

Joint replacement is one of the most common and successful operations in modern orthopedic surgery. It consists of replacing painful, arthritic, worn or diseased parts of the joint with artificial surfaces shaped in such a way as to allow joint movement. Such procedures are a last resort treatment as they are highly invasive and require substantial periods of recovery. Some forms of joint replacement are referred to as total joint replacement indicating that all joint surfaces are replaced. This contrasts with hemiarthroplasty (half arthroplasty) in which only one bone's joint surface is replaced and unicompartmental arthroplasty in which both surfaces of the knee, for example, are replaced but only on the inner or outer sides, not both. Thus, arthroplasty, as a general term, is an operative procedure of orthopedic surgery performed, in which the arthritic or dysfunctional joint surface is replaced with something better or by remodeling or realigning the joint by osteotomy or some other procedure. These procedures are also characterized by relatively long recovery times and are highly invasive procedures. The currently available therapies are not condro-protective. Previously, a popular form of arthroplasty was interpositional arthroplasty with interposition of some other tissue like skin, muscle or tendon to keep inflammatory surfaces apart or excisional arthroplasty in which the joint surface and bone was removed leaving scar tissue to fill in the gap. Other forms of arthroplasty include resection(al) arthroplasty, resurfacing arthroplasty, mold arthroplasty, cup arthroplasty, silicone replacement arthroplasty, etc. Osteotomy to restore or modify joint congruity is also an arthroplasty.

Osteotomy is a related surgical procedure involving cutting of bone to improve alignment. The goal of osteotomy is to relieve pain by equalizing forces across the joint as well as increase the lifespan of the joint. This procedure is often used in younger, more active or heavier patients. High tibial osteotomy (HTO) is associated with a decrease in pain and improved function. However, HTO does not address ligamentous instability—only mechanical alignment. HTO is associated with good early results, but results typically deteriorate over time.

Other approaches to treating osteoarthritis involve an analysis of loads that exist at a joint. Both cartilage and bone are living tissues that respond and adapt to the loads they experience. If a joint surface remains unloaded for appreciable periods of time the cartilage tends to soften and weaken. Further, as with most materials that experience structural loads, particularly cyclic structural loads, both bone and cartilage begin to show signs of failure at loads that are below their ultimate strength. However, cartilage and bone have some ability to repair themselves. There is also a level of load at which the skeleton will fail catastrophically. Accordingly, it has been concluded that the treatment of osteoarthritis and other conditions is severely hampered when a surgeon is not able to precisely control and prescribe the levels of joint load. Furthermore, bone healing research has shown that some mechanical stimulation can enhance the healing response and it is likely that the optimum regime for a cartilage/bone graft or construct will involve different levels of load over time, e.g. during a particular treatment schedule. Thus, there has been identified a need for devices which facilitate the control of load on a joint undergoing treatment or therapy, to thereby enable use of the joint within a healthy loading zone.

Certain other approaches to treating osteoarthritis contemplate external devices such as braces or fixators which control the motion of the bones at a joint or apply cross-loads at a joint to shift load from one side of the joint to the other. Various of these approaches have had some success in alleviating pain but suffer from patient compliance or lack an ability to facilitate and support the natural motion and function of the diseased joint. Notably, the motion of bones forming a joint can be as distinctive as a finger print, and thus, each individual has his or her own unique set of problems to address. Therefore, mechanical approaches to treating osteoarthritis have had limited applications.

Prior approaches to treating osteoarthritis have also been remiss in acknowledging all of the basic functions of the various structures of a joint in combination with its unique movement. That is, in addition to addressing loads at a joint and joint movement, there has not been an approach which also acknowledges the dampening and energy absorption functions of the anatomy, and taking a minimally invasive approach in implementing solutions. Prior devices designed to reduce the load transferred by the natural joint typically describe rigid body systems that are incompressible. Mechanical energy is the product of force (F) and displacement distance (s) of a given mass (i.e., E=F×s, for a given mass M). These systems have zero displacement within their working body (s=0). Since there is no displacement within the device it is reasonable to say that there is no energy storage or absorption in the device. Such devices act to transfer and not absorb energy from the joint. By contrast the natural joint is not a rigid body but is comprised of elements of different compliance characteristics such as bone, cartilage, synovial fluid, muscles, tendons, ligaments, etc. as described above. These dynamic elements act to both transfer and absorb energy about the joint. For example cartilage compresses under applied force and therefore the resultant force displacement product represents the energy absorbed by cartilage. In addition cartilage has a non linear force displacement behavior and is considered viscoelastic. Such systems not only absorb and store, but additionally act to dissipate energy.

Therefore, approaches to treating joint pain are needed that address both joint movement and varying loads as well as energy absorption provided by an articulating joint.

The present invention satisfies these and other needs.

SUMMARY OF THE INVENTION

In accordance with one aspect of the invention, an implantable assembly for manipulating energy transferred by members defining an anatomical joint comprises a first component configured to be attached to a first member of the anatomical joint; a second component configured to be attached to a second member of the anatomical joint; and a hydraulic mechanism joining said first and second components. The hydraulic mechanism includes a first enclosed chamber having at least one elastomeric wall, a second rigid chamber, fluid contained within at least one of said first and second chambers, and a piston sealed with respect to said second rigid chamber and slidable relative thereto. The piston member slides relative to said rigid chamber and said mechanism absorbs energy transferred by said members of the anatomical joint when said first component is attached to said first member and said second component is attached to said second member and a distance between locations of attachment of said first and second components becomes smaller then a predefined distance between said locations.

In accordance with another aspect of the invention, a method for treating an anatomical joint includes attaching a first component of an assembly to a first member of the anatomical joint; and attaching a second component of the assembly to a second member of the anatomical joint, wherein a hydraulic mechanism joins said first and second components; and applying compression to said hydraulic mechanism to absorb load between the first and second members of the anatomical joint.

These and other features of the invention will become apparent to those persons skilled in the art upon reading the details of the assemblies and methods as more fully described below.

BRIEF DESCRIPTION OF THE DRAWINGS

FIG. 1 is a front view, illustrating normal forces existing in a joint.

FIG. 2 is a front view, depicting the effect an energy manipulating assembly of the present invention has on the joint shown in FIG. 1.

FIG. 12A shows a medial side view of an embodiment of an assembly or device according to the present invention installed medially on a knee joint, with the knee joint shown in flexion.

FIG. 12B show a medial side view the embodiment of FIG. 12A with the knee shown in extension.

FIG. 14A illustrates a device installed according to an embodiment of the present invention, using a second extension member having a first curvature.

FIG. 14B illustrates the device of FIG. 14B except where a second extension member having a second curvature different from the first curvature is used.

FIGS. 15A-15B illustrate an embodiment of a hydraulic member according to the present invention, in a first state where a chamber is relatively undeformed, and in a second state where the chamber is deformed, respectively.

DETAILED DESCRIPTION OF THE INVENTION

Figure 3:
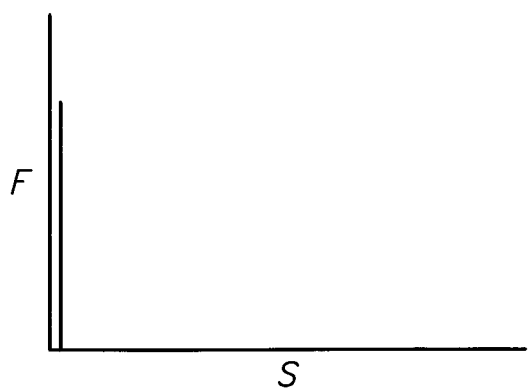
FIG. 3 is a graph, illustrating the energy characteristics of a prior art rigid structure applied across a joint.

Before the present devices/assemblies, mechanisms and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a screw" includes a plurality of such screws and reference to "the component" includes reference to one or more components and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Referring now to the drawings, which are provided by way of example and not limitation, the present invention is directed towards devices and methods for treating body tissues. In applications relating to the treatment of body joints, the present invention seeks to alleviate pain associated with the function of diseased or malaligned members forming a body joint. Whereas the present invention is particularly suited to address issues associated with osteoarthritis, the energy manipulation accomplished by the present invention lends itself well to broader applications. Moreover, the present invention is particularly suited to treating synovial joints such as the knee and shoulder. However, it is also contemplated that the apparatus and method of the present invention can be employed to treat the spine facet joints and spine vertebral joints as well as other synovial and various other joints of the body such as those of the hips, hands and feet.

In one particular aspect, the present invention seeks to permit and complement the unique articulating motion of the members defining a body joint of a patient while simultaneously manipulating energy being experienced by both cartilage and osseous tissue (cancellous and cortical bone). It has been postulated that to minimize pain, off-loading (unloading) or absorption of about 1-40% of forces, in varying degrees, may be necessary. Variable off-loading or absorption in the range of about 5-20% can be a target for certain applications. In certain specific applications, distraction is employed in the energy manipulation approach.

Conventional surgical or minimally invasive surgical approaches are taken to gain access to a body joint or other anatomy requiring attention. Arthroscopic approaches are thus contemplated when reasonable to both implant the energy manipulation assembly as well as to accomplish adjusting an implanted assembly. Moreover, biologically inert materials of various kinds can be employed in constructing the energy manipulation assemblies of the present invention.

In one particular approach, a device is provided in which a hydraulic mechanism is actuated to manipulate or absorb forces between body parts that are joined at a body joint, to which body parts the device is mounted. Thus, a device utilizing a mechanism that can absorb forces applied by the bones that are joined by the joint may be desirable to treat afflictions such as osteoarthritis, trauma, or other pain-causing conditions in a joint.

Referring to FIGS. 1-2, forces occurring between members forming a body joint are described. The arrows 50 shown in FIG. 1 represent forces occurring between adjacent members 6, 7 of a body joint lacking an energy manipulation assembly/device 10 of the present invention. However, in body anatomy incorporating the present invention, less forces are transferred to the bones and cartilage of the members defining the joint. Where the body joint is treated with the foregoing described energy manipulating assemblies of the present invention, a degree of the forces between body members is absorbed by the energy manipulating assembly 10 (depicted as arrows 54 in FIG. 2). Accordingly, less force 56 is placed on the members 6, 7, relative to force 50 placed on member 6, 7 when assembly 10 is not present. Note that although the assembly 10 is schematically represented as being installed on the medial side of the joint shown in FIG. 2, that the present invention is not limited to such an arrangement, as assembly 10 can alternatively be installed on the lateral side of the joint, or a pair of assemblies 10 can alternatively be installed, one on the medial side of the joint and one on the lateral side of the joint.

Figure 4:
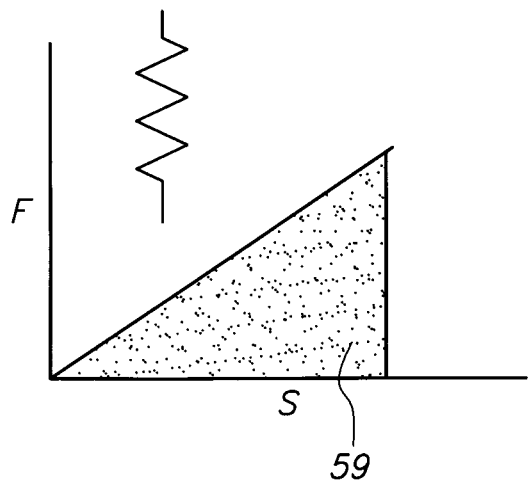
FIG. 4 is a graph, illustrating the energy characteristics of a linear spring system.
Figure 5:
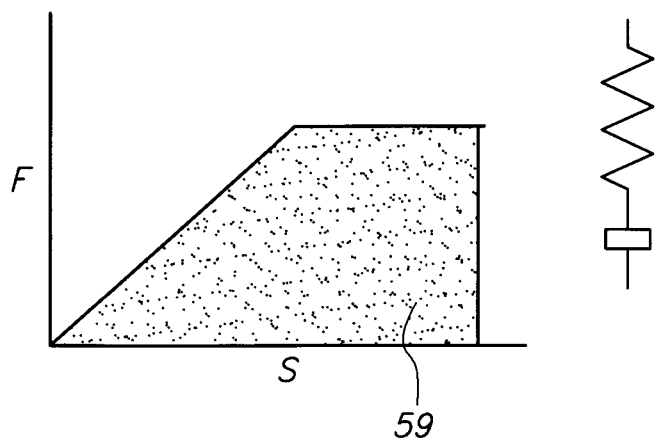
FIG. 5 is a graph, illustrating the energy characteristics of a spring and dampening system.
Figure 6:
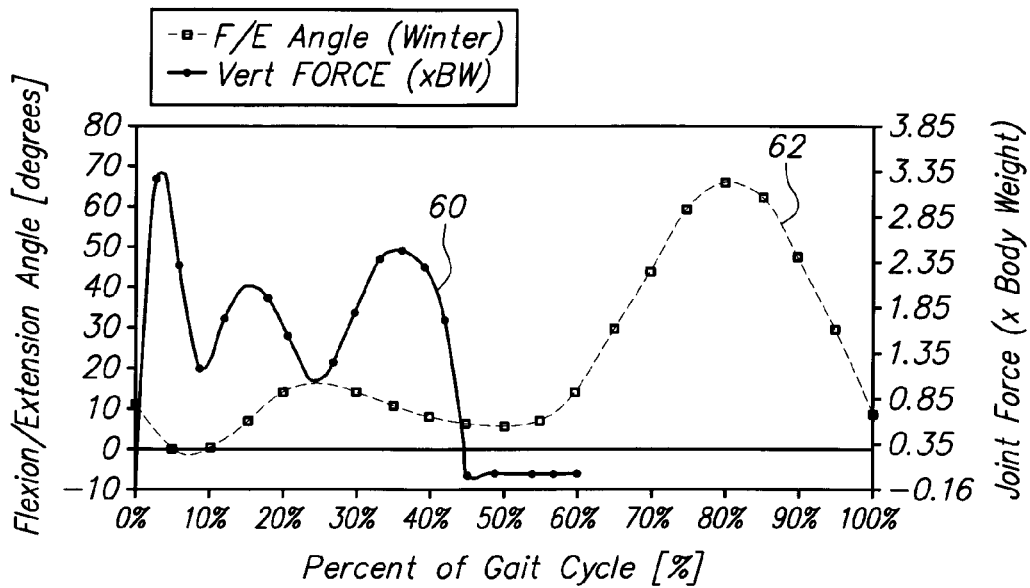
FIG. 6 is a graph, illustrating the flexion/extension angle and joint force existing in a gait cycle.

FIGS. 3-5 illustrate the relation between force (F) and displacement (S) between members of a body joint (where mass is constant). In a rigid body system (FIG. 3) which does not incorporate aspects of the present invention, there is no displacement and no energy absorption. In an energy manipulating system incorporating a single linear spring (FIG. 4), energy is absorbed in proportion to a spring constant (spring stiffness). The energy absorbed is represented by the shaded area 59 below the curve. As shown in FIG. 5, where a spring and dampener is used in combination, the energy absorbed 59 is a function of the spring constant and the dampener. It is these relationships which are considered in developing desired energy manipulating characteristics.

Figure 7:
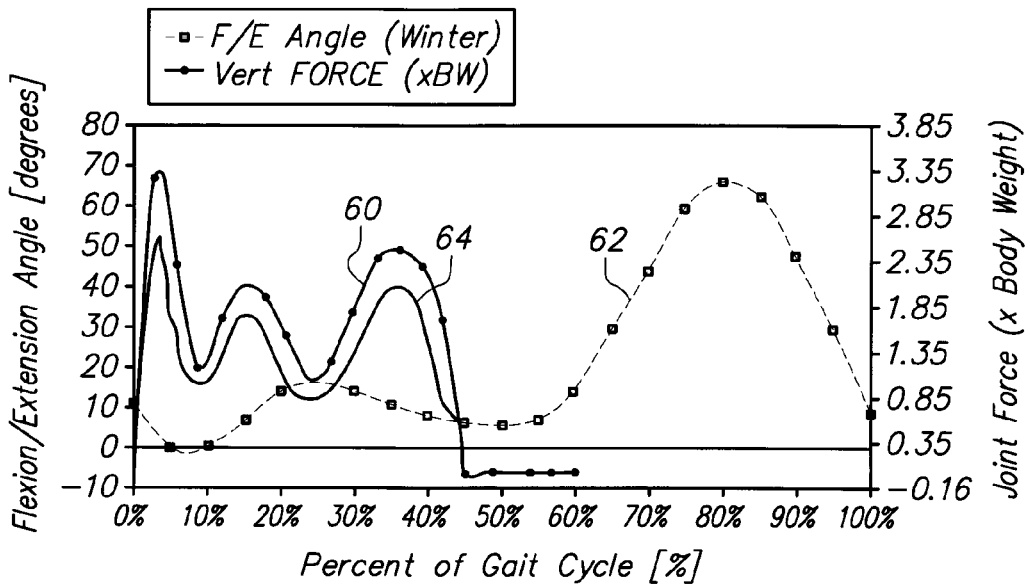
FIG. 7 is a graph, illustrating one approach to energy absorption on a gait cycle.
Figure 8:
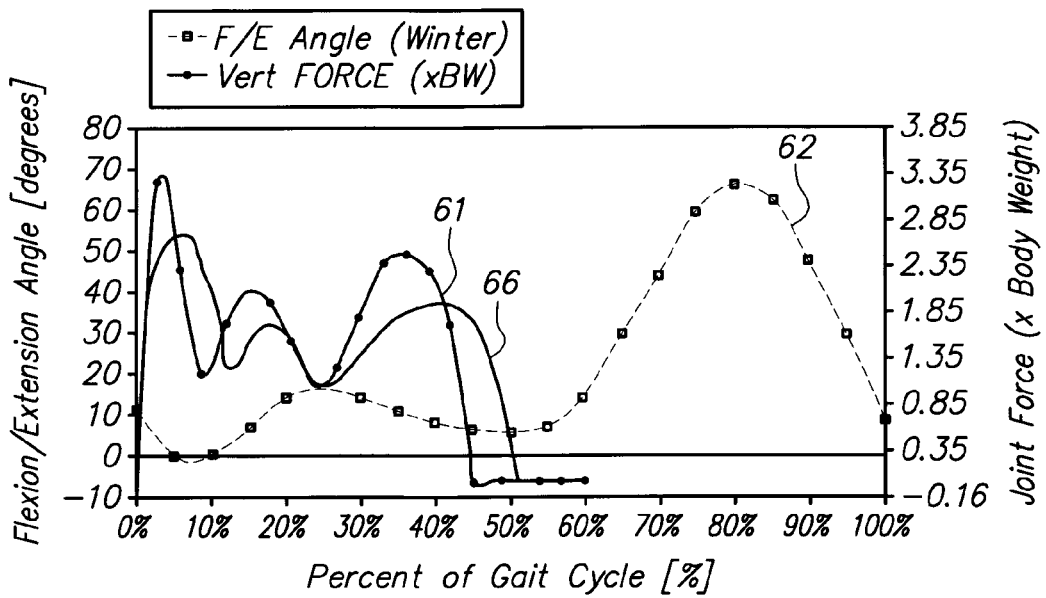
FIG. 8 is a graph, illustrating a second approach to energy absorption on a gait cycle.
Figure 9:
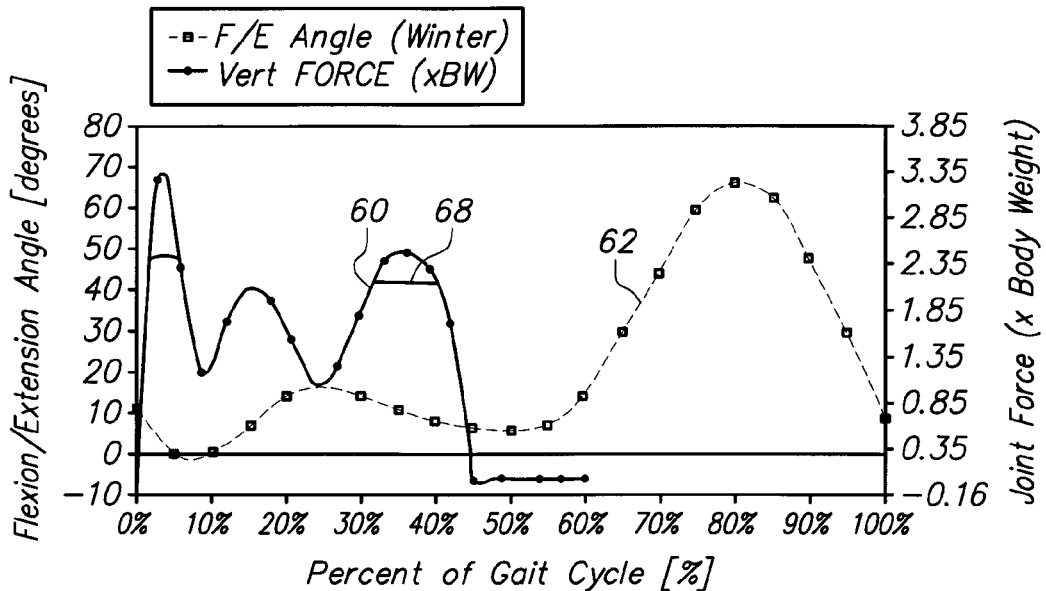
FIG. 9 is a graph, illustrating a third approach to energy absorption on a gait cycle.
Figure 10:
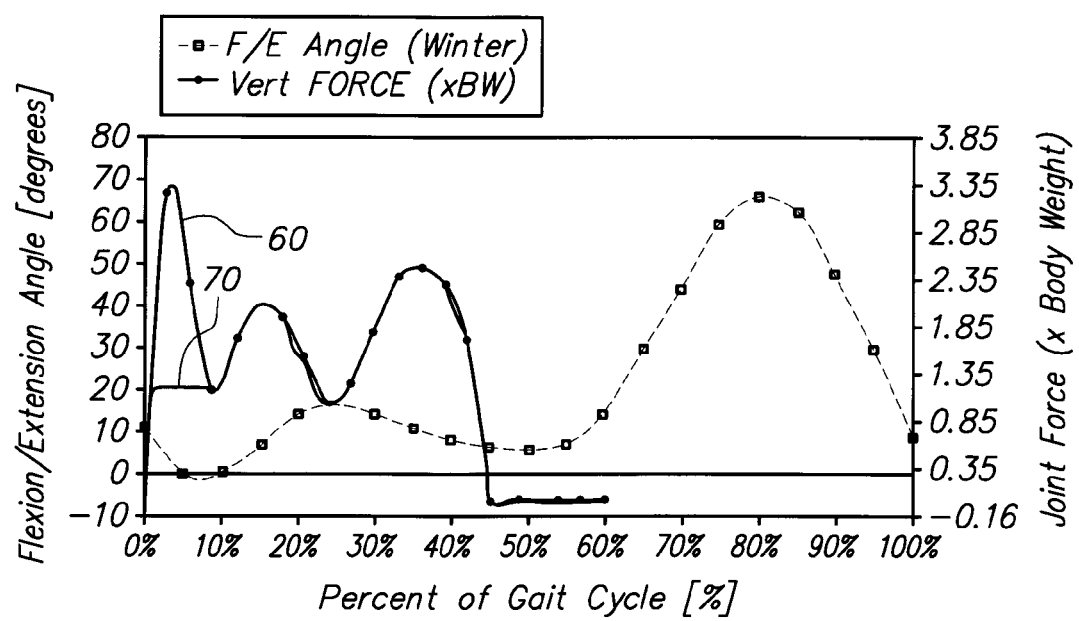
FIG. 10 is a graph, illustrating a fourth approach to energy absorption on a gait cycle.

Also considered are the forces existing through the flexion and extension through an articulation cycle of anatomy to be treated. Using the gait cycle of the legs of a human as an example, both the joint force and flexion/extension angle in degrees can be plotted versus the percentage of the gait cycle completed. A normal or expected relationship 60 of vertical forces generated through the gait cycle is depicted in each of FIGS. 6-10. Also depicted in FIGS. 6-10 is the flexion/extension angle 62. The expected relationship 60 of vertical forces during the gait cycle can be altered using certain of the embodiments of the energy manipulation assemblies of the present invention. As shown in FIG. 7, an energy manipulation assembly 10 according to the present invention can absorb energy by a fixed proportion during a portion of the gait cycle. This is reflected by curve 64. Moreover, energy can be both absorbed and dampened as represented by curve 66 of FIG. 8 or alternatively, energy can be absorbed only above a fixed value as represented by curve 68 of FIG. 9. Additionally, as reflected by curve 70 of FIG. 10, energy can be absorbed in a fixed range of motion. It is to be recognized, however, that each of or one or more of these types of energy absorption can be combined in a desired system.

Figure 11:
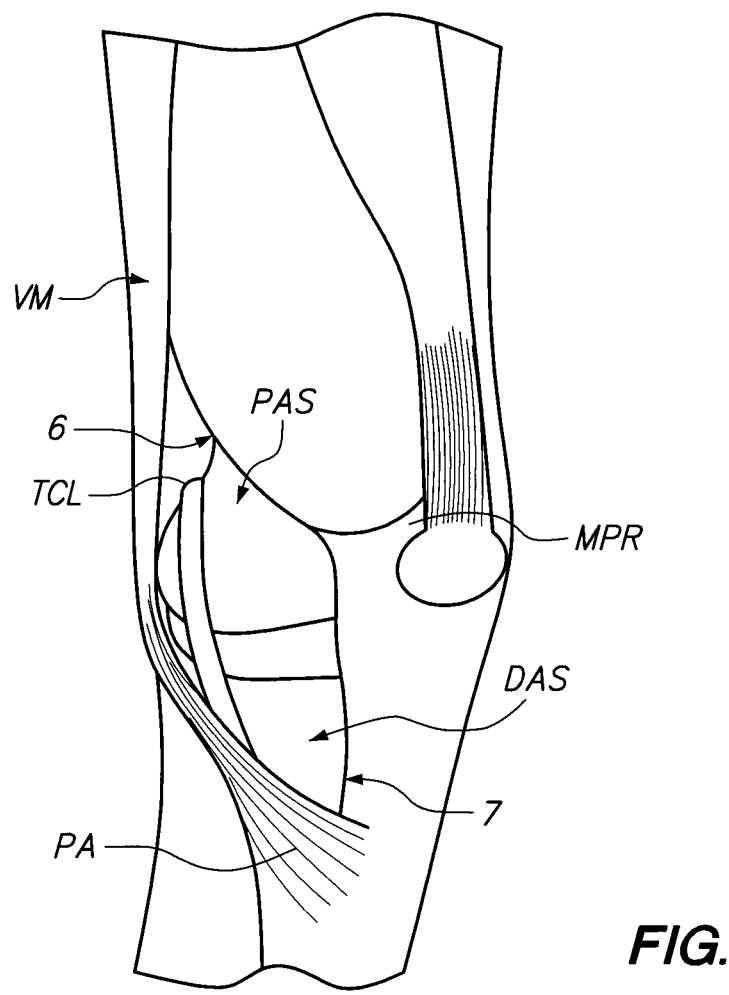
FIG. 11 is a perspective view, depicting anatomy of a typical knee joint.

Referring now to FIG. 11, the medial side anatomy of a typical knee joint is presented in a manner relating to an implantation procedure. Such a procedure could ultimately involve the implantation of devices such as those described below. Although the knee joint is being described here, it is contemplated these devices can also be placed at other joints throughout the body.

In a procedure seeking to off-load or manipulate forces at a knee joint, a proximal attachment site (PAS) for a base component of an energy manipulation device must be identified. Similarly, a distal attachment site (DAS) must also be selected. In a contemplated approach the medial proximal attachment site (PAS) can be located on a femur 6 in a space bounded by the medial patellar retinaculum (MPR), the vastus medialis (VM) and the tibial collateral ligament (TCL). The distal attachment site (DAS) can be located on the tibia in a space between the medial patellar retinaculum (MPR) and the pes anserinus (PA).

FIGS. 12A-12B show a medial side view of an embodiment of an assembly or device 10 according to the present invention installed medially on a knee joint. FIG. 12A shows the knee joint in flexion, with the femur 6 oriented relative to the tibia 7 such that the longitudinal axes of the femur 6 and tibia 7 intersect at about a ninety degree angle. FIG. 12B shows the knee joint in extension, with the femur 6 oriented relative to the tibia 7 such that the longitudinal axes of the femur 6 and tibia 7 are essentially aligned or parallel (0 degrees of flexion).

Assembly/device 10 includes a first component 20 (in this example, first component 20 is a femoral component) and a second component 40 (in this example, second component 40 is a tibial component). The femoral component 20 is configured to be attached to a distal end portion of a patient's femur 6. The first component 20 includes a first base component 22 that is configured to be anchored to a first bone that connects at the joint, and second component 40 includes a second base component 42 that is configured to be anchored to a second bone that connects at the joint.

Figure 13A:
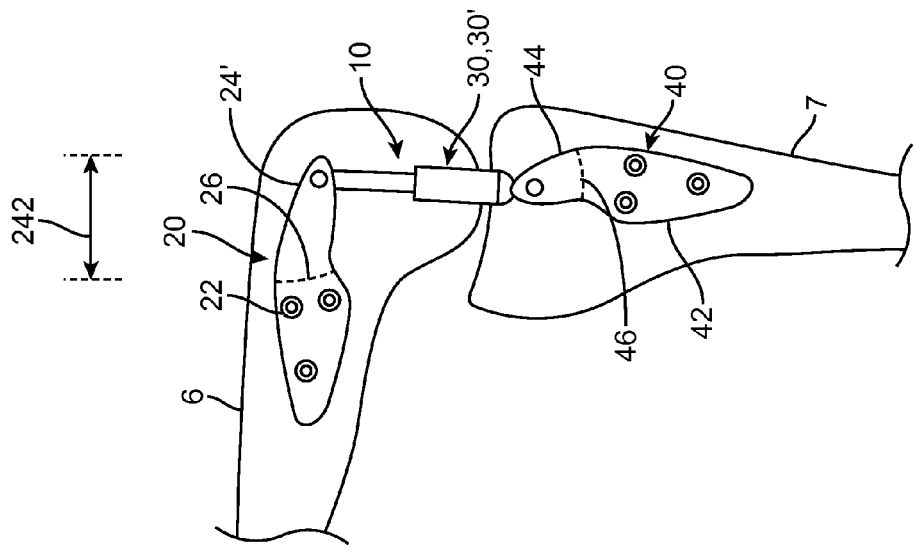
FIG. 13A illustrates a device installed according to an embodiment of the present invention, using a relatively short first extension member.
Figure 13B:
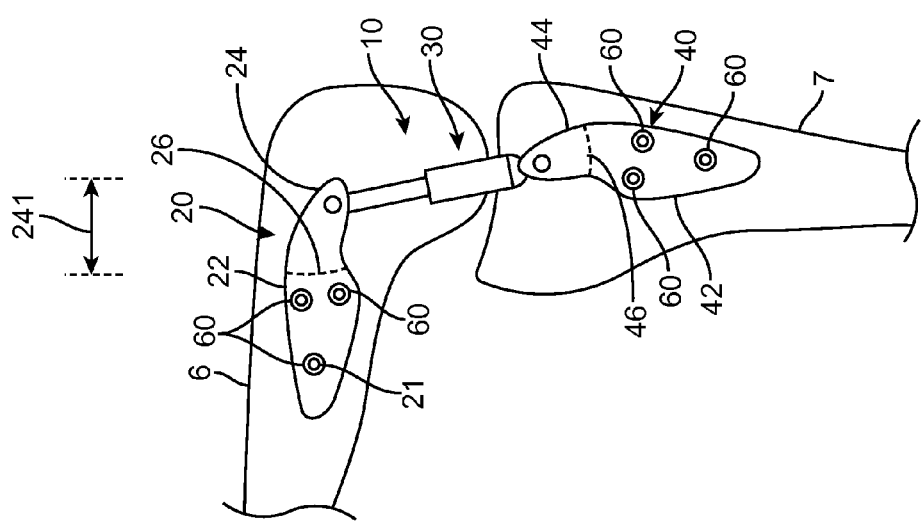
FIG. 13B illustrates the device of FIG. 13A similarly installed as in FIG. 13A, but wherein a relatively longer second extension member has been used.

First component 20 includes a first extension member 24 that may be integral with first base member 22 or may be removably fixed thereto at 26, such as by a dovetail connection with out without locking screw, or other mechanical connection that can be locked during use, but unlocked at any such time as separation of the components 22, 24 is desired. A removably fixed extension member 24 may be preferable for some implantation methods, particularly some minimally invasive methods, although not necessarily required. Also, extension members 24 of varying length may be provided so as to allow some adjustment of the component 20 for alignment purposes, by allowing the installer to interchange extension members 24 of various lengths into the member 20 to achieve the desired alignment and positioning of the member 20 when installed. FIGS. 13A-13B illustrate this principle. In FIG. 13A, when device is installed using the extension member 24 having length 241 like the device in FIG. 12A, the hydraulic mechanism 30 when attached to the extension members 24 and 44 does not axially align with the longitudinal axis of the tibia 7 when the joint is in flexion to the extent that the longitudinal axis of the femur 6 forms a ninety degree angle with the longitudinal axis of the tibia. In this case, this misalignment of the hydraulic member 30 is due to a slightly inaccurately placed fixation location of member 20, which is properly aligned with the femur 6, but not near enough to the distal end of the femur to match the exact target implantation location. In this case, rather that completely removing member 20 and re-implanting it at the correct target location, extension member 24 can be removed and replaced by extension member 24', as shown in FIG. 13B.

By choosing an extension member 24' having length 242 (such as from a set of extension members having varying lengths, for example), the hydraulic mechanism 30 when attached to the extension members 24' and 44 does axially align with the longitudinal axis of the tibia 7 when the joint is in flexion to the extent that the longitudinal axis of the femur 6 forms a ninety degree angle with the longitudinal axis of the tibia, as illustrated in FIG. 13B. Not only does this capability save time during the operation, since it is less time consuming to replace extension member than to remove screws 60, reposition base member 22 and reinstall screws 60 through openings 21 and into new locations in the bone. Perhaps even more importantly, this capability prevents the additional trauma to the bone that occurs when three additional holes are made by replacement of the screws 60. Also, in some instances, there may not be acceptable bone into which to replace the screws at the new target locations.

Likewise, second component 40 includes a second extension member 44 that may be integral with second base member 42 or removably fixed thereto at 46. Similar advantages to those provided to member 24 may be provided by making the second extension member 44 removably fixed to member 42. Likewise, extension members 44 of varying length may be provided so as to allow some adjustment of the component 40 to obtain the proper positioning of the member 40 and particularly the end of member 40 that attaches to hydraulic member 30.

Further in this regard, either of both of second extension member 44 and first extension member 24 may be provided in a set of first or second extension members that, in addition to or alternative to having varying lengths, have variations in shape at the free end portions thereof to vary the lateral location of the connection member 48, 28 relative to the longitudinal axis of the respective member 40, 20. FIGS. 14A-14B illustrate this principle. In FIG. 14A, extension member 44 curves slightly posteriorly from an inferior end thereof to the superior (top) end of the extension member. In the arrangement shown in FIG. 14A, this causes the hydraulic member 30 to be misaligned with the longitudinal axis L2 of the tibia 7 when the joint is flexed at a ninety degree angle and the hydraulic member is interconnected between extension members 24 and 44. By removing the extension member 44 and replacing it with an extension member 44' which has the same length as extension member 44, but curves slightly anteriorly from an inferior end thereof to the superior (top) end of the extension member (see FIG. 14B), this effectively aligns the hydraulic member 30 with the longitudinal axis L2, when the joint is flexed at a ninety degree angle, as shown in FIG. 14B. Further, since the location on extension member 24 where the hydraulic member 30 connects is placed so as to maintain alignment with the longitudinal axis (or to at least minimize movement causing misalignment with the axis L2) over the range of motion of the joint, the hydraulic member 30 remains substantially aligned with the longitudinal axis L2 over the entire range of motion of the joint.

FIGS. 15A-15B illustrate an embodiment of a hydraulic member 30 according to the present invention. The hydraulic member or hydraulic mechanism 30 includes a first connection member 32 configured and dimensioned to be connected to first component 20 (typically at the free end of extension member 24) and a second connection member 34 configured and dimensioned to be connected to second component 40 (typically at the free end of extension member 44). As shown, connection members 32 and 34 are configured as rings or eyelets dimensioned to be screwed or bolted to extension members 24, 44, or linked thereto using a pin that allows relative rotation between the extension member and the connection member, or otherwise linked with alternative fixation elements that allow relative rotation as described. Note also, that the shaft 36 of hydraulic member 30 remains axially rotatable relative to rigid chamber 38 even after the connection members 32, 34 have been connected to the extension members 24, 44. A seal 302 may be provided through which shaft is free to slide and rotate, but which prevents solids and liquids, such as bodily fluids from entering the interior of rigid chamber 38. Piston 306 is provided at an end of shaft 306 and may be integral therewith, as shown, or may be removably fixed to the end of the shaft 306.

An additional chamber 310 is provided within chamber 38 between piston 306 and the closed, rigid end 312 of chamber 310. An incompressible fluid 314 such as saline or other biocompatible liquid is contained within chamber 310 and chamber 310 completely encloses the fluid 314 so that it cannot escape therefrom. The side walls 316 of chamber 310 are rigid enough to maintain the shape of the chamber when no forces are applied thereto, as shown in FIG. 15A, but elastically deform when forces are applied thereto, such as when compressed between piston 306 and end 312 by advancing piston 306 toward end 312, as illustrated in FIG. 15B. At least the side walls 316 of chamber 310 are formed of a biocompatible material that can elastically deform as described, typically an elastomer, but not limited thereto. Upon retraction of the piston, chamber 310 elastically returns to its undeformed shape as illustrated in FIG. 15A.

Because the fluid 314 is incompressible, it applies forces equally in all directions as the piston advances against the chamber 310, as illustrated by the arrows in FIG. 15B. As the chamber 310 elastically deforms, it absorbs energy transferred by the members of the anatomical joint (e.g., femur 6, tibia 7). This deformation of the chamber 310 also provides resistance to compression, thereby dampening the anatomical joint as this motion occurs. This energy absorption and dampening occurs when the piston moves into chamber 38 sufficiently to contact and apply force to chamber 310, and this can be predetermined by where the first and second components 20, 40 are fixed relative to the first and second anatomical members, respectively. Thus, when a distance between locations of attachment of the first and second components becomes smaller then a predefined distance between those locations, the piston 306 is forced against the chamber 310. Additionally, when the piston 306 has compressed the chamber 310 as far as possible (as limited by the incompressibility of the liquid 314 in chamber 310), the mechanism 30 provides a constant unloading force to the first and second anatomical members 6, 7.

Thus the deformable chamber 310, when deformed, provides a counterforce against the piston 306, such that, when piston 306 becomes unloaded or loaded to a lesser degree, the deformable chamber 310 drives the piston in an opposite direction of sliding as the chamber 310 returns toward its undeformed configuration.

Figure 16A:
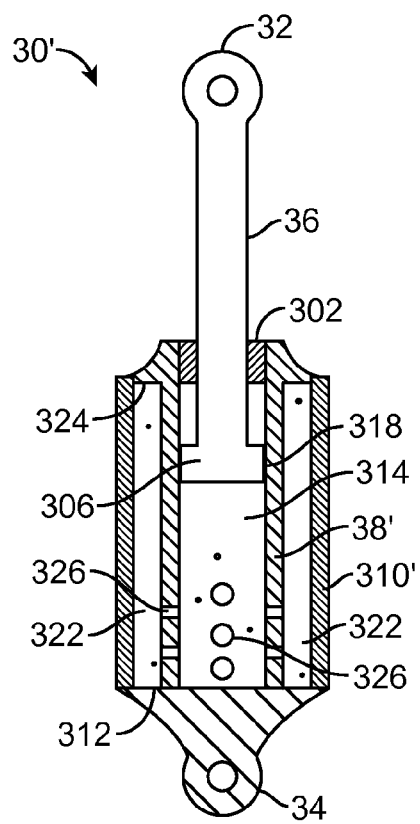
FIGS. 16A-16B illustrate another embodiment of a hydraulic member according to the present invention, in a first state where a chamber is relatively undeformed, and in a second state where the chamber is deformed, respectively.
Figure 16B:
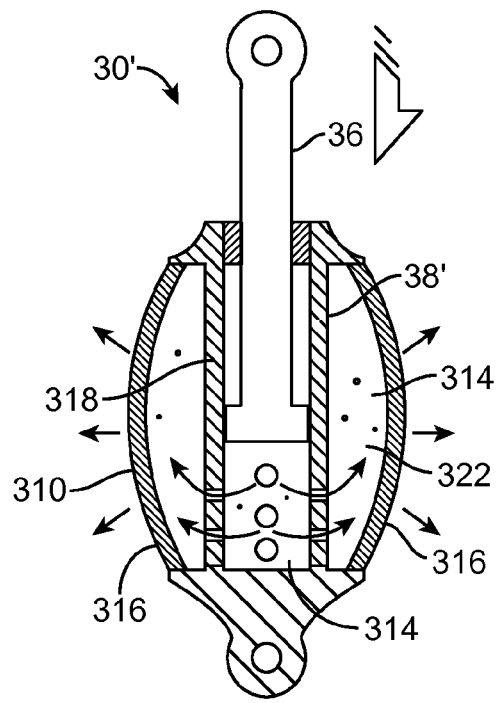

FIGS. 16A-16B illustrate another embodiment of a hydraulic member 30' according to the present invention. The hydraulic member or hydraulic mechanism 30' includes a first connection member 32 configured and dimensioned to be connected to first component 20 (typically at the free end of extension member 24) and a second connection member 34 configured and dimensioned to be connected to second component 40 (typically at the free end of extension member 44). As shown, connection members 32 and 34 are configured as rings or eyelets dimensioned to be screwed or bolted to extension members 24, 44, or linked thereto using a pin that allows relative rotation between the extension member and the connection member, or otherwise linked with alternative fixation elements that allow relative rotation as described. Note also, that the shaft 36 of hydraulic member 30' remains axially rotatable relative to rigid chamber 38' even after the connection members 32, 34 have been connected to the extension members 24, 44. A seal 302 may be provided through which shaft is free to slide and rotate, but which prevents solids and liquids, such as bodily fluids from entering the interior of rigid chamber 38'. Piston 306 is provided at an end of shaft 306 and may be integral therewith, as shown, or may be removably fixed to the end of the shaft 306. Piston 306 is axially slidable and rotatable relative to the inside walls of rigid chamber 38'. However, piston 306 forms a fluid-tight seal with the inner walls of rigid member 38' so that fluid cannot pass between the walls of the chamber 38' and the piston 306 where the piston contacts the walls. This sealing can be enhanced by the use of one or more piston rings (not shown) or other sealing member.

An additional chamber 310' is provided around chamber 38'. Chamber 310' defines an annulus 322 that is formed by the outer walls of chamber 310', lower end 312, upper end 324 and the outer walls of chamber 38' Annulus 322 is completely enclosed except for small openings provided through the walls of chamber 38'. Thus, fluid is prevented from escaping from the annulus 322 out of the mechanism 30', but can flow from chamber 38' to chamber 310'/annulus 222 and vice versa. An incompressible fluid 314 such as saline or other biocompatible liquid is contained within chamber 310' between the free end of the piston 306, end 312 and the inner walls of the chamber 310'. As noted, fluid can be driven, under compression through openings 326 and into annulus/chamber 322. The side walls 318 of chamber 38' are rigid and do not deform even when the piston 306 is advanced against the fluid as illustrated in FIG. 16B. However, when the piston is advanced, it drives fluid through openings 326 and into the annulus 322 of chamber 310' as illustrated in FIG. 16B.

The fluid cannot escape from chamber 310' as noted. However, the walls 316 of chamber 310' elastically deform when the fluid 322 accumulates under pressure therein, having been driven from chamber 38' through openings 326, by advancement of piston 306 toward end 312, as illustrated in FIG. 16B. The side walls 316 of chamber 310' are formed of a biocompatible material that can elastically deform as described.

Typically the side walls are formed of an elastomer, but, other alternative materials that can perform in the same manner (i.e., elastically deform under pressure and then return to the original shape shown in FIG. 16A when piston 306 is withdrawn to the position shown in FIG. 16A). Upon retraction of the piston, the side walls 316 of chamber 310' elastically return to the undeformed shape as illustrated in FIG. 16A, and, in the process, drive fluid 314 from chamber 322 into chamber 38'.

Openings 326 are small so as to provide resistance to flow of the fluid 314 therethrough. Accordingly, mechanism 30' functions as a dampener. For example, in the case where mechanism 30' is used in a device installed across the knee joint (like in FIG. 13B, for example), when the patient is running and therefore piston 306 is pushed relatively quickly against the fluid 314 as the runner's foot impacts the ground, the piston travels a relatively short distance, with relatively less fluid being driven into the chamber 322, as compared to when the piston 306 is pushed slowly, such as in the case where the patient is standing up and standing still, thereby applying a relatively constant force to the piston 306. However, because the chamber 322 is sealed and does not allow liquid to escape therefrom when under pressure from pressurized liquid in chamber 38', the elastic walls 316 of chamber 310' eventually reach a limit such that a steady state is reached as shown in FIG. 16B. Therefore, the mechanism still provides a constant unloading force to the anatomical joint, since the piston 306 is not permitted to sink all the way to the bottom of the chamber 38' under the loading force of the patient's weight during standing. During walking, piston 306 will advance more slowly than during the running example, and dampening will occur at a different rate than while running. Under all these circumstances however, the mechanism 30' of the device 10 maintains an unloading force, since the piston cannot advance all the way to the bottom of the chamber 38'. This unloading force can be predetermined and pre-designed by the amount of liquid 314 in the mechanism, the length of shaft 36, the diameter of the piston 306, the weight of the patient and the relative locations of fixation of the first and second components 20, 40, for example. Other factors to consider for tailoring the unloading force include the elastic properties and thickness of walls 316, as well as the viscosity of the liquid used and the diameter and number of openings 326. When the piston 306 is pushed relatively slowly against the fluid 314, it moves with relatively less resistance thereto, whereas in contrast, when the piston 306 is pushed relatively rapidly against the fluid, the resistance provided by the fluid is relatively greater. In at least one embodiment for use across a knee joint, device 10 was designed to allow up to about 5 mm of compression and produce about forty pounds of unloading of the anatomical knee joint.

Figure 16C:
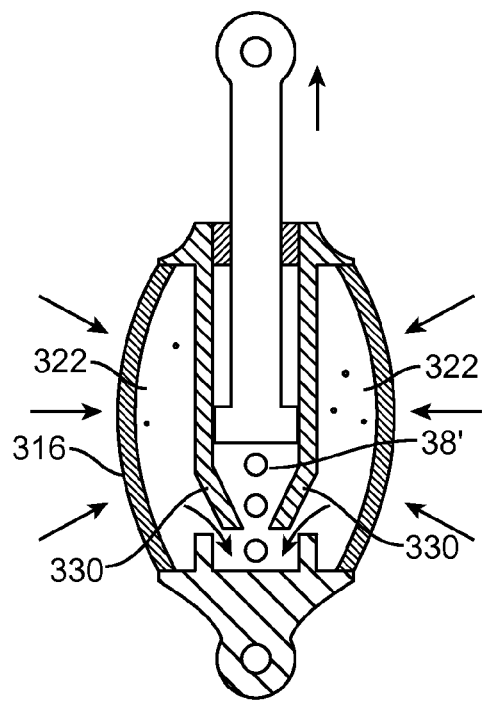
FIG. 16C illustrates a variant of the hydraulic member embodiment shown in FIGS. 16A-16B.

In order to alleviate resistance to flow of the fluid 314 through the openings 326 as it returns from chamber 322 to chamber 38', as driven by the elastic walls returning to their undeformed configurations so as to drive the piston 326 away from the end 312, and thereby allow the driving of the piston back away from the end 312 to occur more rapidly, chamber 38' may optionally be provided with one or more one-way valves 330 therein, as illustrated in FIG. 16C. Each valve 330 allows fluid flow from chamber 322 under pressure into chamber 38' as illustrated in FIG. 16C. The opening of each valve 330 is much larger than the sum of the cross-sectional measurements of openings 326 and therefore fluid 314 can flow under much less resistance and much more rapidly into chamber 38' to return the mechanism to the condition shown in FIG. 16A. Accordingly, when the piston 326 is being pushed toward end 312, the fluid pressure in chamber 38' becomes greater than that in chamber 322 and each valve 330 is forced shut, so that fluid 413 can flow only through openings 326. Valve 330 may be a flapper valve for example, or other type of one-way valve suitable for the described functions.

In at least one embodiment, one or more bones forming the anatomical joint which the assembly/device 10 is to be installed to are three-dimensionally scanned. From the scans of the one or more bones, one or more components of the assembly/device 10 can be custom designed to follow the contours of the one or more bones to which the component(s) is/are to be installed. Whether or not the assembly/device is custom designed, if the components (e.g., 24 and 44 and, optionally 22 and 42) are for temporary implantation, they may be molded components, molded from suitable polymers. Alternatively, the components (e.g., 22, 24, 42 and 44) may be machined from titanium, chromium cobalt alloys, stainless steel, or other biocompatible materials suitable for making implantable braces.

The components 20 and 40 are secured to the bones by one or more fasteners, such as screws, such as locking screws 60, bicortical screws 62, compression screws 64, or the like, passed through openings 21 and screwed into the bones, (e.g., the femur 6 and tibia 7, respectively, as shown in FIG. 12B). Alternative fasteners include, but are not limited to dynamic lag screws.

During loading of the anatomical joint, the forces applied through assembly/device 10 cause hydraulic member 30, 30' to compress by driving piston 306 further into chamber 38, 38'. This results in mechanism 30 taking up (absorbing) the distance change between components under loading of the natural joint. This compression absorbs some of the energy of the forces, thereby reducing the amount of force that is applied through the natural joint, as was described above. Additionally, mechanism 30, 30' can rotate (i.e., piston/shaft 306, 36 rotates relative to chamber 38, 38') to accommodate relative axial rotation between members 20, 40.

During unloading of the anatomical/natural joint, the loading forces are also at least partially removed from piston 306 and unloading forces applied by the elastic walls 316 either directly through chamber 310 or indirectly through liquid 314 drive the piston away from the end 312, as walls 316 return to their undeformed state. Note that in FIGS. 12A-14B, the terminal end portions of the femur 6 and tibia 7 are depicted without surrounding tissue, for purposes of simplicity and clarity. It is noted that the base components 22 and 42 are contoured to match potential mounting surfaces of the femur and tibia. Optionally, assembly 10 can be provided with a subcutaneous tissue barrier in the form of a sheath 58 (e.g., see phantom lines in FIG. 12A), preferably ePTFE, which encloses various parts of the system and excludes surrounding tissue. It is contemplated that the subcutaneous tissue barrier can be formed from or coated alternatively with a tissue in-growth substance or for that matter, substances which inhibit such in-growth. For example, it may be desirable that one or more sides or portions of the assembly 10 enclosed by the sheath 58 be affixed to surrounding tissue whereas it may be advantageous that other portions of the system be free to move with respect to surrounding tissue. Of course, hydraulic member 30, and extension members 24, 44 remain free to move relative to the sheath 58.

FIGS. 12A-12B illustrate that when the anatomical joint (in this case, the knee joint) moves from extension (e.g., FIG. 12B) toward flexion (e.g., FIG. 12A), the bending of the anatomical joint causes extension members 24, 44 to rotate relative to one another. When the anatomical joint moves from flexion (FIG. 12A) toward extension (FIG. 12B), the extension members 24, 44 move back toward their axially aligned configuration like shown in FIG. 12B. Preferably, a point location 36 where relative rotation between extension member 24 and connection member 32 occurs remains substantially axially aligned with extension member 44, and particularly with point location 37 where relative rotation between extension member 44 and connection member 34 occurs, thus maintaining the hydraulic member 30 substantially axially aligned with the tibia 7 throughout the range of motion.

One method for locating a location over which the pivot point 36 (and optionally, pivot point 37 is to be located, is to use imaging equipment to form an image of the knee or other joint being treated, such as by using fluoroscopy and/or three-dimensional navigational software. The members defining the joint are placed in a full lateral position and perpendicularly to the receiver of the imaging device. The proximal joint member is then fixed using a vacuum splint/sandbag or similarly effective device. As one example for implantation to treat the knee joint, the Blumensaat's line of the femur bone 6 can be used as a landmark for locating the various components of the device/assembly 10 so that pivot point 36 is located above a location that is at or near the midpoint of the Blumensaat's line.

Alternatively, it is further contemplated that other regions can represent possible locations of a femoral rotation point on the medial chondyle. In order to select such an alternative point, the surface area of the medial chondyle is mapped to determine regions corresponding to changes in device 10 length of a potentially implanted energy manipulation assembly/device 10 while the joint is moved from full extension to full flexion. Areas of device 10 increasing length and decreasing length can be mapped. Moreover, areas can also be identified where there is an initial device 10 length increase then followed by a length decrease, and where there is an initial length decrease followed by increasing length. Mapping of areas of overlap between these various areas represent transitions from one region to a next. An area representing minimal displacement can also be identified. This information is then employed to identify the various points of rotation best suited for a particular energy manipulation assembly implant 10. The fixation of both bases 22 and 42 are determined by the location of placement of the pivot point locations 36, 37 over the identified area representing minimal displacement.

Furthermore, an approach to proper implant placement can involve observing changes in device length at 90° flexion relative to a fully extended length. These length changes are measured relative to a femoral rotation point at a midpoint of the Blumensaat's line (in the case of a knee joint). The device and rotation point is then selected based upon desired measurement changes. The fixation locations for base 22 on the femur and base 42 on the tibia are then determined by placing the pivot point location 36 over the selected rotation point while the femur 6 and tibia 7 are in full extension, and aligning the bases 22, 42 with the longitudinal axes of the bones 6, 7 respectively. Optionally, a through hole 38 may be provided in each of extension members 24, 44 with the pivot point locations 36,37 serving as the centers of the through holes. In this case, a Kirschner wire (K-wire) can be inserted into the location having been identified to displace minimally over the range of motion of the anatomical joint, and then the extension members can be slid over the K-wire, allowing the K-wire to pass through the holes 38, thereby aligning the pivot point locations 36, 37 with the identified area of minimal displacement.

Likewise, holes 38 can be employed for the other noted methods of locating where, on the bone, the pivots points are to be positioned. For example, a K-wire can be inserted into the femur at about midpoint along the Blumensaat's line.

By maintaining the pivot point 36 over this estimated rotation point (area of minimal displacement) and temporarily fixing bases 22 and 42 at the fixation locations on the femur 6 and tibia 7 dictated by the placement of the pivot point location 36, while the knee joint is in full extension, the knee joint can then be manipulated through its range of motion to simulate the gait cycle and observe the elongation of the assembly 10. The assembly 10 should typically be at its most compressed when the knee joint is in full extension (and thus hydraulic member 30 is at its most elongated) and then should gradually elongate over at least a portion of the gait cycle toward full flexion, while hydraulic member 30 at the same time gradually shortens. The best rotation point can be determined empirically by moving the location of K-wire insertion until the actions of the assembly over the course of the gait cycle have been optimized.

In an alternative approach, a one or more guides may be used such as those described in US Patent Application Publication Nos. 2008/0275561, 2009/0014016 and 2011/0112639 which are hereby incorporated by reference in their entirety.

Each of the embodiments described herein can incorporate or cooperate with sensing mechanisms adapted to provide loading information concerning the tissues being treated. Thus, it is contemplated that the various pressure sensing mechanisms available can be placed upon the devices of the present invention. Such sensors can be configured to provide information about the efficacy of the energy manipulating device of the present invention and whether adjustments are necessary. Similarly, sensors can be placed on anatomy to provide information regarding loads being placed on the tissues themselves.

Furthermore, it is contemplated that drugs can be delivered to the interventional site targeted for energy manipulation. In this regard, the entirety of the subject matter disclosed in U.S. Publication No. 2007/0053963 is hereby incorporated herein, by reference thereto.

The energy absorbing assemblies 10 of the present invention can be surface mounted upon anatomy or can be inserted completely or partially within the target tissue.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. An implantable assembly for manipulating energy transferred by members defining an anatomical joint, the members collectively defining a path of motion, said assembly comprising:

a first component configured to be attached to a first member of the anatomical joint;

a second component configured to be attached to a second member of the anatomical joint; and a hydraulic mechanism joining said first and second components;

wherein said hydraulic mechanism includes a first enclosed chamber having at least one elastomeric wall, a second rigid chamber, fluid contained within at least one of said first and second chambers, and a piston sealed with respect to said second rigid chamber and slidable relative thereto, wherein said piston slides relative to said rigid chamber and said mechanism absorbs energy transferred by said members of the anatomical joint when said first component is attached to said first member and said second component is attached to said second member and a distance between locations of attachment of said first and second components becomes smaller then a predefined distance between said locations.

2. The assembly of claim 1, wherein said mechanism provides dampening during relative movement between said first and second components when said distance between locations of attachment of said first and second components is smaller than said predefined distance, and said mechanism provides a constant unloading force to said components when said distance between locations of attachment of said first and second components remains constant and is smaller than said predefined distance.

3. The assembly of claim 1, wherein said fluid is sealed within said first enclosed chamber.

4. The assembly of claim 3, wherein said first enclosed chamber is contained within said second rigid chamber.

5. The assembly of claim 4, wherein said piston is slidable against said first enclosed chamber to deform said first enclosed chamber, and whereby deformation of said at least one elastomeric wall absorbs energy inputted thereto by said piston to deform said at least one elastomeric wall.

6. The assembly of claim 5, wherein said at least one elastomeric wall, when deformed, provides a counterforce against said piston, such that, when said piston becomes unloaded or loaded to a lesser degree, said at least one elastomeric wall drives said piston in an opposite direction of sliding as said at least one elastomeric wall returns toward an undeformed configuration.

7. The assembly of claim 1, wherein said first enclosed chamber at least partially surrounds said second rigid chamber.

8. The assembly of claim 1, wherein said first enclosed chamber is external of, and in fluid communication with said second rigid chamber.

9. The assembly of claim 8, wherein said second rigid chamber contains a least a portion of said fluid and said second rigid chamber comprises at least one small hole through said chamber that provides resistance to flow but allows flow of said fluid therethrough under pressure.

10. The assembly of claim 9, wherein said at least one elastomeric wall of said first chamber deforms as said first chamber receives said fluid through said at least one small hole and becomes pressurized.

11. The assembly of claim 10, wherein said at least one elastomeric wall, when deformed, provides back pressure against said fluid in said second chamber and against said piston, wherein, when said piston becomes static relative to said second chamber while under load transferred thereto from said first and second anatomical members, said back pressure prevents sliding of said piston past a predetermined location relative to said second chamber, thereby preventing expulsion of all fluid from said second chamber and providing a constant unloading force.

12. The assembly of claim 9, wherein said second chamber comprises a one-way valve that prevents flow of said fluid out of said second chamber but allows flow of said fluid into said second chamber.

13. The assembly of claim 12, wherein said one-way valve provides low resistance to flow, relative to the resistance to flow provided by said at least one small opening.

14. The assembly of claim 1, wherein said mechanism, when connected to said first and second components, permits relative axial rotations between said first and second components.

15. The assembly of claim 1, wherein the anatomical joint is a knee joint, said first component is adapted to be fixed to a femur of the knee joint and second component is adapted to be fixed to a tibia of the knee joint.

16. The assembly of claim 1, wherein said hydraulic mechanism compresses and absorbs energy from the forces applied by the members of the anatomical joint, thereby relieving at least a portion of the load resultant form the forces from being transferred through contacting surfaces of the anatomical joint.

17. The assembly of claim 1, wherein said assembly relieves load on a side of the anatomical joint to which said assembly is attached.

* * * * *